(12) United States Patent
You et al.

(10) Patent No.: US 11,808,749 B2
(45) Date of Patent: Nov. 7, 2023

(54) METHOD OF ESTIMATING CHEMICAL OXYGEN DEMAND OF WATER

(71) Applicant: National Yang Ming Chiao Tung University, Hsinchu (TW)

(72) Inventors: Sheng-Mu You, Miaoli County (TW); Ruey-An Doong, Hsinchu County (TW)

(73) Assignee: NATIONAL YANG MING CHIAO TUNG UNIVERSITY, Hsinchu (TW)

( * ) Notice: Subject to any disclaimer, the term of this patent is extended or adjusted under 35 U.S.C. 154(b) by 0 days.

(21) Appl. No.: 17/931,552

(22) Filed: Sep. 13, 2022

(65) Prior Publication Data

US 2023/0003707 A1 Jan. 5, 2023

Related U.S. Application Data

(62) Division of application No. 16/425,930, filed on May 29, 2019, now Pat. No. 11,474,091.

(30) Foreign Application Priority Data

Jun. 4, 2018 (TW) ................................. 107119214

(51) Int. Cl.
*G01N 33/18* (2006.01)
*G01N 31/22* (2006.01)
(Continued)

(52) U.S. Cl.
CPC ......... *G01N 33/1806* (2013.01); *G01N 31/22* (2013.01); *G01N 21/78* (2013.01); *G01N 2035/00683* (2013.01)

(58) Field of Classification Search
CPC ......... G01N 2035/00683; G01N 31/22; G01N 31/225; G01N 33/1806; G01N 21/77; G01N 21/78; G01N 21/01
(Continued)

(56) References Cited

U.S. PATENT DOCUMENTS

| 3,540,845 A | 11/1970 | Hickey |
| 5,415,809 A * | 5/1995 | Elson ..................... G01N 21/78 436/1 |

(Continued)

FOREIGN PATENT DOCUMENTS

| CN | 1719233 A | 1/2006 |
| CN | 101074924 A | 11/2007 |

(Continued)

OTHER PUBLICATIONS

Yu. M. Dedkov et al., "Dichromate method for the determination of chemical oxygen demand," Journal of Analytical Chemistry, vol. 55, No. 8, 2000.

(Continued)

*Primary Examiner* — Maureen Wallenhorst
(74) *Attorney, Agent, or Firm* — CKC & Partners Co., LLC

(57) ABSTRACT

The present disclosure provides a color chart and a test kit for estimating chemical oxygen demand of water. The color chart includes a blue component, an indigo component, an umber component, and an orange component. The test kit includes an oxidant, a reductant, an indicator, and the color chart. The present disclosure also provides a method for estimating chemical oxygen demand of water. The method includes providing a water sample; adding an oxidant to the water sample; heating the water sample; adding a reductant to the water sample; adding an indicator to the water sample, such that the water sample develops a color; and matching the color of the water sample with the color components of the color chart to estimate the chemical oxygen demand of the water sample.

6 Claims, 2 Drawing Sheets

(51) Int. Cl.
 *G01N 21/78* (2006.01)
 *G01N 35/00* (2006.01)

(58) Field of Classification Search
 USPC .................................... 436/62, 164; 422/79
 See application file for complete search history.

(56) References Cited

U.S. PATENT DOCUMENTS

| | | | | |
|---|---|---|---|---|
| 5,556,787 | A | * | 9/1996 | Miller ................ G01N 33/1806 436/166 |
| 6,967,104 | B2 | | 11/2005 | Kalia et al. |
| 8,101,136 | B2 | * | 1/2012 | Kalia ..................... G01N 21/75 436/127 |
| 11,474,091 | B2 | * | 10/2022 | You ........................ G01N 31/22 |
| 2005/0191753 | A1 | | 9/2005 | Kalia et al. |

FOREIGN PATENT DOCUMENTS

| | | |
|---|---|---|
| CN | 101713739 A | 5/2010 |
| CN | 101750414 A | 6/2010 |
| CN | 102288599 A | 12/2011 |
| CN | 103278501 A | 9/2013 |
| CN | 104655790 A | 5/2015 |
| CN | 104792775 A | 7/2015 |
| CN | 105445413 A | 3/2016 |
| CN | 105548160 A | 5/2016 |
| CN | 106932532 A | 7/2017 |
| CN | 107764958 A | 3/2018 |
| TW | M496760 U | 3/2015 |

OTHER PUBLICATIONS

A. F. Gaudy et al., "A Colorimetric Method for Determining Chemical Oxygen Demand," Journal (Water Pollution Control Federation), vol. 36, No. 12, Dec. 1964.

* cited by examiner

METHOD OF ESTIMATING CHEMICAL OXYGEN DEMAND OF WATER

CROSS-REFERENCE TO RELATED APPLICATION

The present application is a Divisional Application of the U.S. application Ser. No. 16/425,930, filed May 29, 2019, now U.S. Pat. No. 11,474,091, granted on Oct. 18, 2022, which claims priority to Taiwan Application Serial Number 107119214, filed Jun. 4, 2018, which is herein incorporated by reference.

BACKGROUND

Field of Invention

The present disclosure relates to a color chart, a test kit and a method of estimating chemical oxygen demand of water and wastewater.

Description of Related Art

The higher the content of organic compounds in water, the greater the degree of water pollution. Chemical oxygen demand (COD) is an important indicative measure for measuring the organic compounds content in water. COD is defined as the required oxygen equivalents to oxidize reducing substances in each liter of water sample and is expressed in unit of milligrams per liter (mg/L).

In the conventional method of estimating chemical oxygen demand of a water sample, the water sample has to be brought to a laboratory in order to perform a heating process and a reflow process for two hours. The total duration to estimate COD of a water sample is usually greater than three hours considering the time required for water sample pretreatment and titration. Therefore, the conventional method of estimating chemical oxygen demand is time-consuming, and the chemical oxygen demand test result of the water sample cannot be obtained on-site and in a short time.

In summary, there is a need for a tool and method for on-site rapid screening of chemical oxygen demand to provide instant and rapid understanding of the organic compounds concentration in water and wastewater.

SUMMARY

The present disclosure provides a color chart for estimating chemical oxygen demand of water. The color chart includes a blue component specified as PANTONE 2387C, an indigo component specified as PANTONE 2111XGC, an umber component specified as PANTONE 2350C, and an orange component specified as PANTONE 1788XGC.

In one embodiment, the color chart further includes a numeric sign "50" corresponding to the blue component.

In one embodiment, the color chart further includes a numeric sign "100" corresponding to the indigo component.

In one embodiment, the color chart further includes a numeric sign "150" corresponding to the umber component.

In one embodiment, the color chart further includes a numeric sign "200" corresponding to the orange component.

In one embodiment, the color chart further includes a dark blue component specified as PANTONE 288C.

In one embodiment, the color chart further includes a numeric sign "75" corresponding to the dark blue component.

In one embodiment, the color chart further includes a brown component specified as PANTONE 4625C.

In one embodiment, the color chart further includes a numeric sign "125" corresponding to the brown component.

The present disclosure also provides a test kit for estimating chemical oxygen demand of water. The test kit includes an oxidant, a reductant, an indicator, and the aforementioned color chart.

In one embodiment, the oxidant includes potassium dichromate.

In one embodiment, the reductant includes ammonium iron(II) sulfate.

In one embodiment, the indicator includes a ferrion indicator.

The present disclosure also provides a method of estimating chemical oxygen demand of water. The method includes providing a water sample; adding an oxidant to the water sample; heating the water sample; adding a reductant to the water sample; adding an indicator to the water sample, such that the water sample develops a color; and matching the color of the water sample with a plurality of color components of a color chart to estimate a chemical oxygen demand of the water sample.

In one embodiment, the oxidant includes potassium dichromate.

In one embodiment, the reductant includes ammonium iron(II) sulfate.

In one embodiment, the indicator includes a ferrion indicator.

In one embodiment, the step of heating the water sample includes heating the water sample to 90° C. to 110° C.

In one embodiment, the step of heating the water sample includes heating the water sample for 8 minutes to 15 minutes.

In one embodiment, the color components include a blue component, an indigo component, an umber component, and an orange component. The blue component is specified as PANTONE 2387C and corresponds to a numeric sign "50". The indigo component is specified as PANTONE 2111XGC and corresponds to a numeric sign "100". The umber component is specified as PANTONE 2350C and corresponds to a numeric sign "150". The orange component is specified as PANTONE 1788XGC and corresponds to a numeric sign "200".

In one embodiment, the color components further include a dark blue component. The dark blue component is specified as PANTONE 288C and corresponds to a numeric sign "75".

In one embodiment, the color components further include a brown component. The brown component is specified as PANTONE 4625C and corresponds to a numeric sign "125".

In summary, the present disclosure provides a tool for on-site rapid estimation of chemical oxygen demand of water. The color chart and the test kit in the present disclosure enable the operator to obtain the test result of chemical oxygen demand of water in a short time. The present disclosure also provides a test method can be carried out on-site for rapid screening of chemical oxygen demand of water.

BRIEF DESCRIPTION OF THE DRAWINGS

The disclosure can be more fully understood by reading the following detailed description of the embodiment, with reference made to the accompanying drawings as follows.

DETAILED DESCRIPTION

The following disclosure provides many different embodiments, or examples, for implementing different features of the provided subject matter. Specific examples of components and arrangements are described below to simplify the present disclosure. These are, of course, merely examples and are not intended to be limiting. The embodiments disclosed in the following may be combined or substituted with each other in an advantageous situation, and other embodiments may be added in an embodiment without further description or explanation. In the following description, details will be given. The specific details are set forth to enable the reader to fully understand the following embodiments. However, the embodiments of the present disclosure may be practiced without the specific details.

Some embodiments of the present disclosure are described in detail below, but the present disclosure is not limited to the scope of the embodiment.

Figure 1:
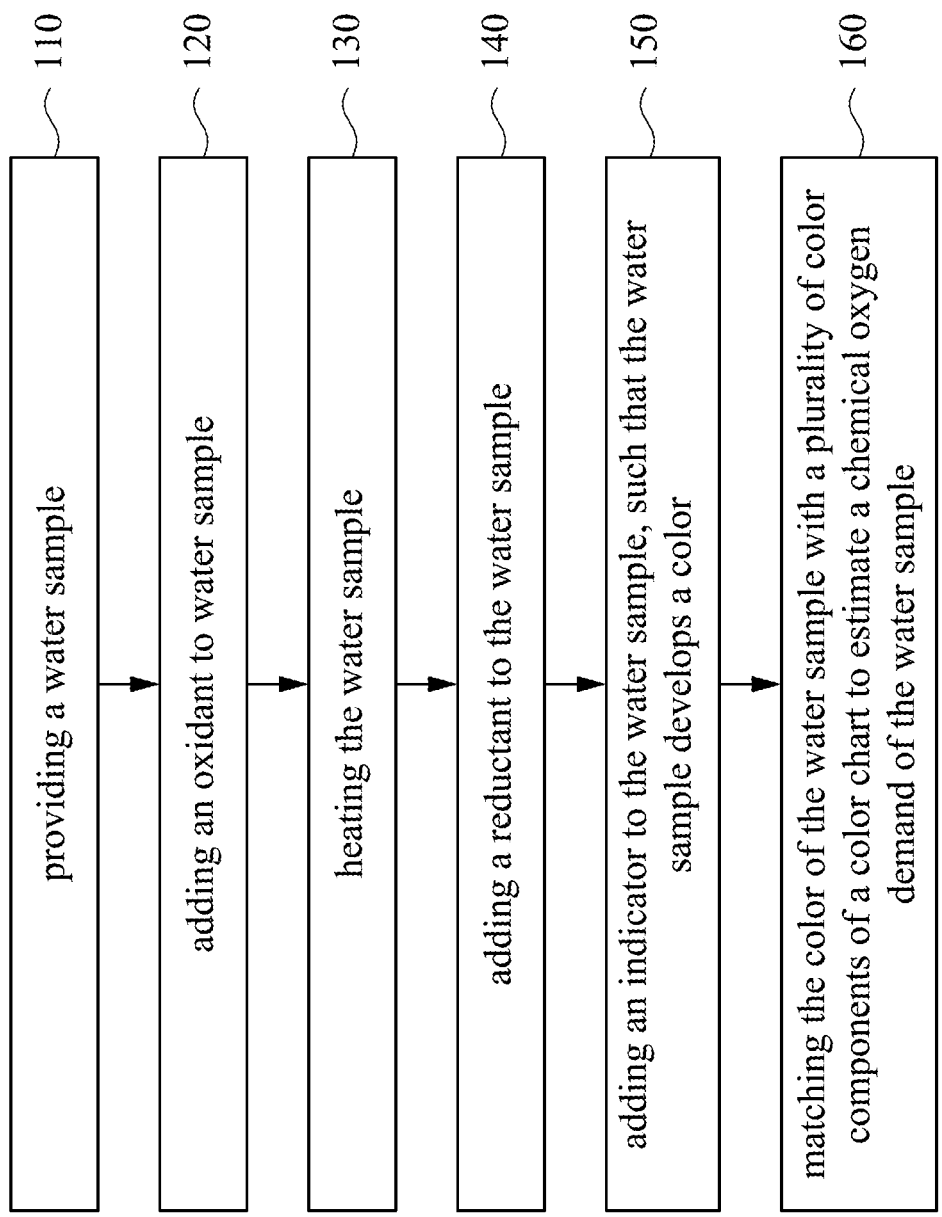
FIG. 1 depicts a flow chart of a method for estimating chemical oxygen demand of water according to some embodiments of the present disclosure.

Reference is made to FIG. 1. FIG. 1 depicts a flow chart of a method 100 for estimating chemical oxygen demand of water according to some embodiments of the present disclosure. The method 100 includes step 110, step 120, step 130, step 140, step 150, and step 160.

At step 110, a water sample is provided. It is understood that the water sample may include water bodies in any environmental system, such as domestic wastewater, industrial wastewater, agriculture wastewater, livestock wastewater, river water, sea water, rainwater, and the like. In one embodiment, a sample volume of the water sample ranges from 0.5 ml to 10 ml, such as 1 ml, 1.5 ml, 3 ml, 5 ml, or 8 ml. In one embodiment, the water sample may be transported to a test tube after the water sample is drawn up by using a micropipette. In one embodiment, the water sample may be centrifuged to separate impurities in the water sample, such that the water sample may have a clear and transparent appearance.

At step 120, an oxidant is added to the water sample. Specifically, the chemical oxygen demand is an index for measuring the organic compounds content in water. Since most organic compounds are reducing agent, and thus the organic compounds can be oxidized by an oxidant and then decomposed into compounds of smaller molecular weights. In one embodiment, the oxidant includes potassium dichromate. Potassium dichromate is a strong oxidant which is capable to oxidize a number of reducing substances, and the hexavalent chromium is reduced to the trivalent chromium state. Therefore potassium dichromate may oxidize the organic compounds in a water sample, and the hexavalent chromium of potassium dichromate is reduced to trivalent chromium. On the other hand, if there is no organic compound in a water sample or the organic compounds in the water sample have been completely consumed by potassium dichromate, the excess hexavalent chromium of the potassium dichromate will remain in the water sample. In one embodiment, potassium dichromate is an excess reagent with a concentration ranges from 0.01 M to 0.05 M, such as 0.025 M. In one embodiment, a volume of potassium dichromate ranges from 0.25 ml to 5 ml, such as 0.5 ml, 0.75 ml, 1.5 ml, 2.5 ml, or 4 ml. In one embodiment, a strong acid is added to the water sample. The strong acid may be such as a concentrated sulfuric acid solution which provides an acidic environment and thereby enhancing the oxidizing ability of the oxidant to the organic compounds in the water sample. A volume of the concentrated sulfuric acid solution may range from 0.5 ml to 10 ml, such as 1 ml, 1.5 ml, 3 ml, 5 ml, or 8 ml. In one embodiment, a sulfuric acid solution containing mercury(II) sulfate may be optionally added to the water sample. The sulfuric acid solution containing mercury(II) sulfate may have a concentration of 0.05 M and a volume ranges from about 0.5 ml to 10 ml, such as 1 ml, 1.5 ml, 3 ml, 5 ml, or 8 ml. The sulfuric acid solution containing mercury(II) sulfate may diminish the background interference which arise from the oxidation of chloride ions by potassium dichromate in the water sample.

At step 130, the water sample is heated. In one embodiment, the water sample is heated to 90° C. to 110° C., such as 95° C., 98° C., 100° C., 102° C., 105° C., or 108° C. If the heating temperature is lower than 90° C., the reaction rate of the redox reaction between the oxidant and the organic compounds in the water sample may be low. If the heating temperature is higher than 110° C., the volatilization of volatile organic compounds in the water sample may be promoted, such that the volatile organic compounds may evaporate from the water sample, causing errors in COD estimation. In one embodiment, the water sample is heated for 8 minutes to 15 minutes, such as 9 minutes, 11 minutes, 13 minutes, or 14 minutes. If the heating time is less than 8 minutes, the organic compounds in the water sample cannot be completely oxidized by the oxidant. If the heating time is greater than 15 minutes, the duration will be too long. In one embodiment, the water sample may be heated by a portable heater.

At step 140, a reductant is added to the water sample. In one embodiment, the reductant includes an ammonium iron(II) sulfate solution. In one embodiment, a concentration of the ammonium iron(II) sulfate solution may range from 0.02 M to 0.2 M, such as 0.025 M or 0.125 M. In one embodiment, a volume of a solution of ammonium iron(II) sulfate may range from 0.15 ml to 3 ml, such as 0.3 ml, 0.45 ml, 0.9 ml, 1.5 ml, or 2.4 ml.

At step 150, an indicator is added to the water sample, such that the water sample develops a color. In one embodiment, the indicator includes a ferrion indicator. In one embodiment, the ferrion indicator may be prepared by mixing 1,10-phenanthroline and iron(II) sulfate. In one embodiment, a ratio of the reductant to the indicator ranges from 4:1 to 2:1, more preferably is 3:1, such that the water sample may develop a visible color. In one embodiment, a volume of the ferrion indicator may range from 0.05 ml to 1 ml, such as 0.1 ml, 0.15 ml, 0.3 ml, 0.5 ml, or 0.8 ml.

Specifically, after the indicator is added to the water sample, the water sample may develop different colors depending on the chemical oxygen demand content of the water sample. For example, after adding the indicator to a water sample with a chemical oxygen demand of 50 mg/L, the water sample may develop a blue color. Similarly, a water sample with a chemical oxygen demand 75 mg/L, 100 mg/L, 125 mg/L, 150 mg/L, or 200 mg/L may develop a dark blue color, an indigo color, a brown color, an umber color, or an orange color respectively after the indicator is added thereto. Further, the correspondence between the color of the water sample and the chemical oxygen demand content of the water sample as provided in the present disclosure is unprecedented.

Figure 2:
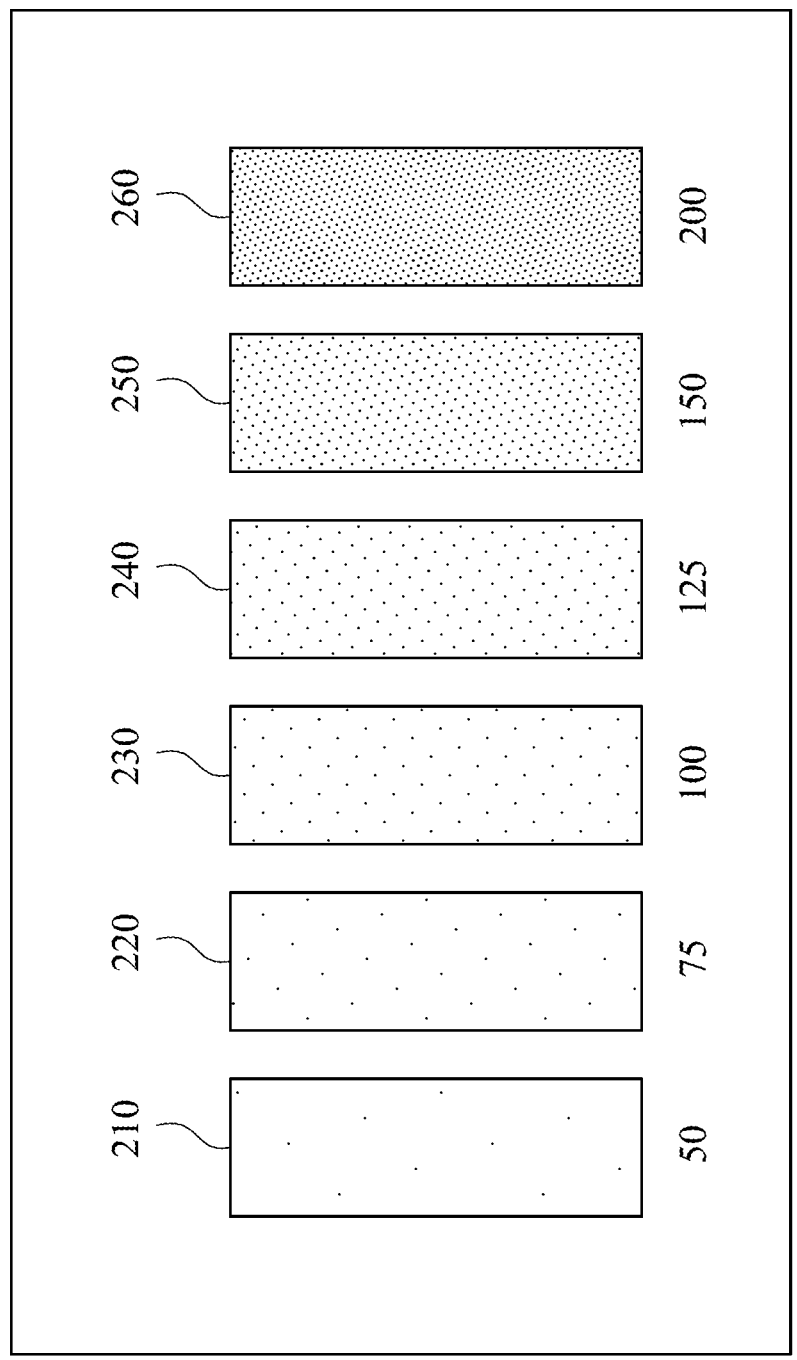
FIG. 2 depicts a schematic view of a color chart for estimating chemical oxygen demand of water according to some embodiments of the present disclosure.

At step 160, the color of the water sample is matched with a plurality of color components of the color chart in order to estimate the chemical oxygen demand of the water sample. Reference is now made to FIG. 2. FIG. 2 depicts a schematic view of a color chart 200 according to one embodiment of the present disclosure. The color components of the color chart 200 include a blue component 210, a dark blue component 220, an indigo component 230, a brown component 240, an umber component 250, and an orange component 260. In one embodiment, the blue component 210 is specified as PANTONE 2387C and corresponds to a numeric sign "50". In one embodiment, the dark blue component 220 is specified as PANTONE 288C and corresponds to a numeric sign "75". In one embodiment, the indigo component 230 is specified as PANTONE 2111XGC and corresponds to a numeric sign "100". In one embodiment, the brown component 240 is specified as PANTONE 4625C and corresponds to a numeric sign "125". In one embodiment, the umber component 250 is specified as PANTONE 2350C and corresponds to a numeric sign "150". In one embodiment, the orange component 260 is specified as PANTONE 1788XGC and corresponds to a numeric sign "200".

When the COD estimation of a water sample is conducted on site, an operator can estimate the COD of the water sample readily by matching the color of the water sample with the color components of the color chart 200 and then read out the corresponding numeric sign of the color component. Therefore, the operator can obtain the estimation result of chemical oxygen demand in a short time.

In addition, the color components of the color chart 200 in the present disclosure may allow the operator to perform color matching without much difficulty. Specifically, regarding the color components of the color chart 200, the blue component, the dark blue component and the indigo component are a cool color, while the brown component, the umber component, and the orange component are a warm color. Therefore the visual difference between the cool color and warm color may allow the operator to match the color readily with the naked eye.

It is understood that the method 100 of the present disclosure is a rapid-screening method, and therefore the COD test result is an interval instead of an exact value.

The present disclosure also provides a test kit of estimating chemical oxygen demand of water. The test kit includes an oxidant, a reductant, an indicator, and the color chart 200.

In one embodiment, the oxidant includes potassium dichromate which serves as an excess reagent, and the concentration of potassium dichromate ranges from 0.01 M to 0.05 M, such as 0.025 M. A volume of potassium dichromate may range from 0.25 ml to 5 ml, such as 0.5 ml, 0.75 ml, 1.5 ml, 2.5 ml, or 4 ml.

In one embodiment, the reductant includes an ammonium iron(II) sulfate solution. A concentration of the ammonium iron(II) sulfate solution may range from 0.02 M to 0.2 M, such as 0.025 M or 0.125 M. A volume of the ammonium iron(II) sulfate solution may range from 0.15 ml to 3 ml, such as 0.3 ml, 0.45 ml, 0.9 ml, 1.5 ml, or 2.4 ml.

In one embodiment, the indicator includes a ferrion indicator. In one embodiment, a volume ratio of the reductant to the indicator ranges from 4:1 to 2:1, more preferably is 3:1, such that the water sample may develop a visible color. The ferrion indicator may be prepared by mixing 1,10-phenanthroline with iron(II) sulfate. A volume of the ferrion indicator may range from 0.05 ml to 1 ml, such as 0.1 ml, 0.15 ml, 0.3 ml, 0.5 ml, or 0.8 ml.

In one embodiment, the color chart 200 may have a plurality of color components including a blue component 210, a dark blue component 220, an indigo component 230, a brown component 240, an umber component 250, and an orange component 260. In one embodiment, the blue component 210 is specified as PANTONE 2387C and corresponds to a numeric sign "50". In one embodiment, the dark blue component 220 is specified as PANTONE 288C and corresponds to a numeric sign "75". In one embodiment, the indigo component 230 is specified as PANTONE 2111XGC and corresponds to a numeric sign "100". In one embodiment, the brown component 240 is specified as PANTONE 4625C and corresponds to a numeric sign "125". In one embodiment, the umber component 250 is specified as PANTONE 2350C and corresponds to a numeric sign "150". In one embodiment, the orange component 260 is specified as PANTONE 1788XGC and corresponds to a numeric sign "200".

The following examples are provided to illustrate certain aspects of the present disclosure and to aid those of skill in the art in practicing this disclosure. These examples are in no way to be considered to limit the scope of the disclosure in any manner.

Example 1—Defining the Color of a Series of Standard Solutions

In Example 1, the standard solutions include a series of 1 ml of potassium hydrogen phthalate (KHP) solutions with a known COD of 50 mg/L, 75 mg/L, 100 mg/L, 125 mg/L, 150 mg/L, or 200 mg/L respectively. The step 120 to step 150 of the method 100 were performed on each standard solution, and the color developed by each standard solution were defined.

Specifically, 0.5 ml of 0.025 M potassium dichromate and 1 ml of concentrated sulfuric acid solution were added to each standard solution and heated to 100° C. for 10 minutes. Next, 0.3 ml of 0.025 M ammonium iron(II) sulfate solution and 0.1 ml of ferrion indicator were added to each standard solution sequentially, such that each standard solution developed a color. The ferrion indicator was prepared by diluting 1.485 g of 1,10-phenanthroline and 0.695 g of iron(II) sulfate by reagent water to 100 ml. The color of each standard solution was matched with the color code of PANTONE color system to define the color of each standard solution, and the results are shown in Table 1.

TABLE 1

| COD of standard solution (mg/L) | Color | Pantone color code |
| --- | --- | --- |
| 50 | blue | 2387C |
| 75 | dark blue | 288C |
| 100 | indigo | 2111XGC |
| 125 | brown | 4625C |
| 150 | umber | 2350C |
| 200 | orange | 1788XGC |

Next, the defined colors were set as color components of a color chart, and each color component has a corresponding numeric sign. Specifically, each numeric sign represents the COD of the standard solution having the color, i.e., 50 mg/L, 75 mg/L, 100 mg/L, 125 mg/L, 150 mg/L, and 200 mg/L.

Example 2

Example 2 is COD estimation of sewage drainage wastewater (i.e., domestic wastewater). The color of each water sample in Example 2 was matched with the color component of the color chart in Example 1. In addition, the COD test results in Example 2 were further compared with the COD test results obtained by Standard Method NIEA W515.54A promulgated by the Environmental Protection Administration, Executive Yuan, R.O.C. to verify the accuracy of the COD test results obtained by the method of the present disclosure. It is understood that the method of the present disclosure is a rapid-screening method, and thus the COD test results are interval instead of exact values.

Example 2 provided eight water samples of sewage drainage wastewater, which were named as Sample A1 through Sample A8 with a volume of 1 ml for each sample. 0.5 ml of 0.025 M potassium dichromate and 1 ml of concentrated sulfuric acid solution were added to the water sample and heated to 100° C. for 10 minutes. 0.3 ml of 0.025 M ammonium iron(II) sulfate solution was added to the water sample. Next, 0.1 ml of ferrion indicator was added to the water sample, such that each water sample developed a color. The ferrion indicator was prepared by diluting 1.485 g of 1,10-phenanthroline and 0.695 g of iron(II) sulfate with reagent water to 100 ml. The color of each water samples was matched with the color component of the color chart to estimate the COD of each water sample.

The COD of Sample A1 through Sample A8 were estimated by the method 100 of the present disclosure and Standard Method NIEA W515.54A promulgated by the Environmental Protection Administration, Executive Yuan, R.O.C. The estimated COD of Sample A1 through Sample A8 are listed in Table 2.

TABLE 2

| Sample | Color | Pantone color code | COD interval estimated by the method of the present disclosure (mg/L) | COD estimated by Standard Method NIEA W515.54A (mg/L) |
|---|---|---|---|---|
| A1 | blue | 2387C | <50 | 18.9 |
| A2 | blue | 2387C | <50 | 21.3 |
| A3 | blue | 2387C | <50 | 42.5 |
| A4 | between blue and dark blue | 2387C, 288C | 50-75 | 52 |
| A5 | between blue and dark blue | 2387C, 288C | 50-75 | 59.3 |
| A6 | between blue and dark blue | 2387C, 288C | 50-75 | 60.9 |
| A7 | Between brown and umber | 4625C, 2350C | 125-150 | 130 |
| A8 | orange | 1788XGC | >200 | 238 |

According to the COD test results as shown in Table 2, the method of the present disclosure is able to provide an excellent COD estimation for sewage drainage wastewater. Specifically, each color developed by Sample A1 to Sample A3 was visually close to PANTONE 2387C, and therefore the COD of Sample A1 to Sample A3 were estimated to be 0-50 mg/L. According to the test results of the standard method, the COD of Sample A1 through Sample A3 was 18.9 mg/L, 21.3 mg/L and 42.5 mg/L respectively, and they were within the interval of 0-50 mg/L as estimated by the method of the present disclosure.

Each color of Sample A4 to Sample A6 was between blue and dark blue and was visually close to PANTONE 2387C and PANTONE 288C. Therefore the COD of Sample A4 to Sample A6 were estimated to be 50-75 mg/L. According to the test results of the standard method, the COD of Sample A4 to Sample A6 was 52 mg/L, 59.3 mg/L and 60.9 mg/L respectively, and they were within the interval of 50-75 mg/L as estimated by the method of the present disclosure.

The color of Sample A7 was between brown and umber and was visually close to PANTONE 4625C and PANTONE 2350C. Therefore the COD of Sample A7 was estimated to be 125-150 mg/L. According to the test results of the standard method, the COD of Sample A7 was 130 mg/L, which was within the interval of 125-150 mg/L as estimated by the method of the present disclosure.

The color of Sample A8 was an orange color visually close to PANTONE 1788XGC, and therefore the COD of Sample A8 was estimated to be greater than 200 mg/L. According to the test results of the standard method, the COD of Sample A8 was 238 mg/L, which was greater than 200 mg/L as estimated by the method of the present disclosure.

Example 3

The procedure of Example 3 was basically the same as Example 2, except that the samples of Example 3 were industrial wastewater collected from several industrial wastewater discharges. Specifically, the sources of the wastewater include food processing industry (Sample B1), petrochemical industry (Sample B2 to Sample B4), dyeing and finishing industry (Sample B5 to Sample B7), metal surface plating industry (Sample B8 to Sample B10), and printed circuit board processing industry (Sample B11 to Sample B13).

The COD of Sample B1 to Sample B13 were estimated by the method 100 of the present disclosure and Standard Method NIEA W515.54A promulgated by the Environmental Protection Administration, Executive Yuan, R.O.C. The COD test results of Sample B1 to Sample B13 are listed in Table 3.

TABLE 3

| Sample | Color | Pantone color code | COD interval estimated by the method of the present disclosure (mg/L) | COD estimated by Standard Method NIEA W515.54A (mg/L) |
|---|---|---|---|---|
| B1 | orange | 1788XGC | >200 | 6010 |
| B2 | blue | 2387C | <50 | 18.6 |
| B3 | between dark blue and indigo | 288C, 2111XGC | 75-100 | 80.6 |
| B4 | orange | 1788XGC | >200 | 1070 |
| B5 | blue | 2387C | <50 | 34 |
| B6 | between blue and dark blue | 2387C, 288C | 50-75 | 60.7 |
| B7 | between brown and umber | 4625C,2350C | 125-150 | 124 |
| B8 | blue | 2387C | <50 | 3.1 |
| B9 | blue | 2387C | <50 | 10.8 |
| B10 | blue | 2387C | <50 | 20.4 |
| B11 | blue | 2387C | <50 | 12.6 |
| B12 | blue | 2387C | <50 | 15.6 |
| B13 | blue | 2387C | <50 | 41.5 |

According to the COD test results in Table 3, each COD interval of Sample B11 to Sample B13 estimated by the method of the present disclosure is consistent with the COD test results obtained from the standard method respectively. In other words, the method of the present disclosure is able to provide an excellent COD estimation for various industrial wastewater as well, such as food processing industry (see Sample B1), petrochemical industry (see Sample B2 to Sample B4), dyeing and finishing industry (see Sample B5 to Sample B7), metal surface plating industry (see Sample B8 to Sample B10), and printed circuit board processing industry (see Sample B11 to Sample B13).

Example 4

The procedure of Example 4 was basically the same as Example 2, except that the samples of Example 4 were river water collected from different rivers. The samples of Example 4 were named as Sample C1 through Sample C5.

The COD of Sample C1 to Sample C5 were estimated by the method 100 of the present disclosure and Standard Method NIEA W515.54A promulgated by the Environmental Protection Administration, Executive Yuan, R.O.C. The COD test results of Sample C1 to Sample C5 are listed in Table 4.

TABLE 4

| Sample | Color | Pantone color code | COD interval estimated by the method of the present disclosure (mg/L) | COD estimated by Standard Method NIEA W515.54A (mg/L) |
|---|---|---|---|---|
| C1 | blue | 2387C | <50 | 26.3 |
| C2 | blue | 2387C | <50 | 17.3 |
| C3 | blue | 2387C | <50 | 18.3 |
| C4 | between blue and dark blue | 2387C, 288C | 50-75 | 88.3 |
| C5 | blue | 2387C | <50 | 23.3 |

According to the COD test result in Table 4, each COD interval of Sample C1 to Sample C5 estimated by the method of the present disclosure is consistent with the COD test results obtained from the standard method COD respectively. In other words, the method of the present disclosure is able to provide an excellent COD estimation for river water as well.

In summary, the present disclosure provides a chemical oxygen demand estimation tool for on-site rapid-screening of chemical oxygen demand. The color chart and the test kit of the present disclosure may allow the operator to obtain the test results on-site and in a short time. The present disclosure also provides a chemical oxygen demand estimation method for on-site rapid screening.

Although the present invention has been described in considerable detail with reference to certain embodiments thereof, other embodiments are possible. Therefore, the spirit and scope of the appended claims should not be limited to the description of the embodiments contained herein.

It will be apparent to those skilled in the art that various modifications and variations can be made to the structure of the present invention without departing from the scope or spirit of the invention. In view of the foregoing, it is intended that the present invention cover modifications and variations of this invention provided they fall within the scope of the following claims.

What is claimed is:

1. A method of estimating chemical oxygen demand of water, comprising steps of:
    providing a water sample;
    adding an oxidant to the water sample after providing the water sample, wherein the oxidant is potassium dichromate, and a concentration of the potassium dichromate ranges from 0.01 M to 0.05 M;
    heating the water sample after adding the oxidant to the water sample;
    adding a reductant to the water sample after heating the water sample, wherein the reductant is ammonium iron(II) sulfate, and a concentration of the ammonium iron(II) sulfate ranges from 0.02 M to 0.2 M;
    adding an indicator to the water sample after heating the water sample, such that the water sample develops a color, wherein the indicator is a ferrion indicator, and a ratio of the reductant to the indicator ranges from 4:1 to 2:1; and
    matching the color of the water sample with a plurality of color components of a color chart after adding the reductant to the water sample and adding the indicator to the water sample to estimate a chemical oxygen demand of the water sample, wherein each of the plurality of color components has a corresponding numeric sign representing the chemical oxygen demand of the water sample.

2. The method of claim 1, wherein the step of heating the water sample comprises heating the water sample to 90° C.-110° C.

3. The method of claim 1, wherein the step of heating the water sample comprises heating the water sample for 8 minutes to 15 minutes.

4. The method of claim 1, wherein the color components comprise:
    a blue component;
    an indigo component;
    an umber component; and
    an orange component.

5. The method of claim 4, wherein the color components further comprise a dark blue component.

6. The method of claim 5, wherein the color components further comprises a brown component.

* * * * *